(12) United States Patent
Kamiya et al.

(10) Patent No.: US 8,737,563 B2
(45) Date of Patent: May 27, 2014

(54) RADIATION IMAGING SYSTEM, CONSOLE, AND RADIATION IMAGING PROGRAM

(75) Inventors: Takeshi Kamiya, Kanagawa (JP);
Yusuke Kitagawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 737 days.

(21) Appl. No.: 12/929,379

(22) Filed: Jan. 20, 2011

(65) Prior Publication Data
US 2011/0235782 A1    Sep. 29, 2011

(30) Foreign Application Priority Data

Mar. 24, 2010  (JP) .................................. 2010-068894

(51) Int. Cl.
*G01N 23/083* (2006.01)
*H05G 1/64* (2006.01)

(52) U.S. Cl.
USPC .................... 378/62; 378/96.8; 250/370.09

(58) Field of Classification Search
USPC ........... 378/62, 91, 98, 98.8, 189; 250/370.09
See application file for complete search history.

(56) References Cited

U.S. PATENT DOCUMENTS

| | | | |
|---|---|---|---|
| 7,239,685 B2 * | 7/2007 | Petrick et al. ................. | 378/116 |
| 7,250,608 B2 * | 7/2007 | Ozeki ...................... | 250/370.08 |
| 7,365,337 B2 * | 4/2008 | Tsuchino et al. ......... | 250/370.09 |
| 7,545,914 B2 * | 6/2009 | Kito et al. .................... | 378/98.8 |
| 7,593,507 B2 * | 9/2009 | Ohta et al. .................... | 378/98.8 |
| 7,655,916 B2 * | 2/2010 | Ohta et al. ............... | 250/370.08 |
| 7,737,427 B2 * | 6/2010 | Kito et al. ..................... | 250/580 |
| 7,767,981 B2 * | 8/2010 | Kuwabara et al. ......... | 250/484.4 |
| 7,772,560 B2 * | 8/2010 | Ohta et al. ............... | 250/370.09 |
| 7,777,193 B2 * | 8/2010 | Kito et al. ................ | 250/370.09 |
| 7,974,382 B2 * | 7/2011 | Kitano et al. .................. | 378/114 |
| 8,053,727 B2 * | 11/2011 | Nishino et al. ............. | 250/336.1 |
| 8,149,116 B2 * | 4/2012 | Nishino et al. ................ | 340/540 |
| 2006/0215892 A1 | 9/2006 | Ohara | |

FOREIGN PATENT DOCUMENTS

| | | |
|---|---|---|
| JP | 2005006979 A | 1/2005 |
| JP | 2007151999 A | 6/2007 |
| JP | 2010035778 A | 2/2010 |
| WO | WO-2006103790 A1 | 10/2006 |
| WO | WO-2008099644 A1 | 8/2008 |

* cited by examiner

*Primary Examiner* — Allen C. Ho
(74) *Attorney, Agent, or Firm* — Jean C. Edwards, Esq.; Edwards Neils PLLC (57) ABSTRACT

A radiation imaging system has a radiation generation device, an FPD cassette, and a console. The console judges whether or not the FPD cassette is in a good communication state repeatedly once every thirty seconds. Upon receiving a radiography order, the console changes repetition intervals from thirty seconds to three seconds, and keeps judging the communication state of the FPD cassette. The repeated judgment is continued until a shutter button is pressed. Upon the press of the shutter button, the radiation generation device emits radiation to carry out radiography.

8 Claims, 8 Drawing Sheets

RADIATION IMAGING SYSTEM, CONSOLE, AND RADIATION IMAGING PROGRAM

CROSS-REFERENCE TO RELATED APPLICATIONS

The present application claims priority from Japanese Patent Application No. 2010-068894, filed Mar. 24, 2010, the contents of which are herein incorporated by reference in their entirety.

BACKGROUND OF THE INVENTION

1. Field of the Invention

The present invention relates to a radiation imaging system having a flat panel detector and a console, and a radiation imaging program.

2. Description Related to the Prior Art

In a medical field, a radiation imaging system that uses radiation such as X-rays is widely known. The radiation imaging system is constituted of a radiation generation device for applying the radiation to a patient's body part to be examined, and a radiation detection device for detecting the radiation that has passed through the body part. As the radiation detection device, an imaging plate (IP) contained in an IP cassette and a flat panel detector (FPD) are in practical use. The FPD has the advantage that can directly convert the radiation into image data. Moreover, a portable FPD cassette that contains the FPD in a casing of the same shape and size as those of the IP cassette is recently developed to allow loading of the FPD on the conventional radiation imaging system.

For example, United States Patent Application Publication No. 2006/0215892 discloses a radiation imaging system that includes the FPD cassette having a battery and an antenna, and a console for establishing communication with the FPD cassette by radio. In this radiation imaging system, an operating state of the FPD cassette is checked occasionally, at the time of establishing a correspondence between the FPD cassette and the console, at the time of reception of a radiography order by the console, and the like.

In response to the reception of the radiography order, radiography is generally started after precise positioning of the FPD cassette. During preparation for the radiography, the FPD cassette sometimes becomes unavailable due to battery exhaustion or failure caused by electrostatic charge by a touch of a doctor or shock by a drop. In these cases, it is necessary to prohibit application of the radiation and to notify the doctor of unavailability of the FPD cassette, for the purpose of preventing unnecessary exposure of the patient to the radiation.

Also, before the reception of the radiography order, the FPD cassette sometimes becomes unavailable in a like manner due to the battery exhaustion or the failure caused by the electrostatic charge or the shock. In these cases, it is desirable to inform the doctor as soon as possible of unavailability of the FPD cassette, because the FPD cassette needs exchange.

To afford convenience to the doctor, it is conceivable to repeatedly carry out an operation check of the FPD cassette at regular time intervals. However, the operation check requires the FPD cassette to communicate with the console. Consequently, periodic repetition of the operation check causes increase in battery consumption of the FPD cassette, and shortens battery life thereof.

SUMMARY OF THE INVENTION

An object of the present invention is to provide a radiation imaging system that repeatedly carries out an operation check of an FPD cassette at required time intervals with minimizing battery consumption of the FPD cassette.

To achieve the above and other objects of the present invention, a radiation imaging system according to the present invention includes a radiation imaging cassette and a console. The radiation imaging cassette has a radiation detector for detecting radiation and producing image data, and a data sending section for sending various types of data including the image data by radio. The console has an order receiving section for receiving an order for radiography, a data receiving section for receiving the image data sent from the data sending section of the radiation imaging cassette, a judgment section for repeatedly judging an operating state of the radiation imaging cassette, and an interval determiner for determining a repetition interval of the judgment by the judgment section. The interval determiner sets the repetition interval at a first time interval, before the order receiving section receives the order. On the contrary, the interval determiner sets the repetition interval at a second time interval, after the order receiving section receives the order. The first time interval is longer than the second time interval.

It is preferable that the judgment section judge a communication state between the radiation imaging cassette and the console, as the operating state of the radiation imaging cassette.

The radiation imaging cassette may further include a thermometer for measuring a temperature inside a casing. The data sending section of the radiation imaging cassette sends the temperature measured by the thermometer to the console. The judgment section judges the operating state of the radiation imaging cassette based on the temperature.

If the temperature is within a predetermined range, the judgment section may judge that the radiation imaging cassette is in a good operating state.

When the radiography is started, the interval determiner may command the judgment section to suspend the judgment. When at least first one screen of the image data out of plural screens of the image data obtained by the radiography is sent from the radiation imaging cassette to the console, the interval determiner may command the judgment section to restart the judgment at the first time intervals. Otherwise, when all the plural screens of the image data are sent from the radiation imaging cassette to the console, the interval determiner may command the judgment section to restart the judgment at the first time intervals.

A radiation imaging program according to the present invention makes a computer of the console execute the steps of repeatedly judging an operating state of a radiation imaging cassette, receiving an order for radiography, setting a repetition interval of the judgment at a first time interval before the reception of the order, setting the repetition interval of the judgment at a second time interval that is shorter than the first time interval after the reception of the order, and carrying out the radiography by the radiation imaging cassette in accordance with the order.

According to the present invention, the repetition interval at which the operating state of the radiation imaging cassette is repeatedly judged is set longer before the reception of the radiography order, as compared with that after the reception of the radiography order. Thus, before the reception of the radiography order, the number of the judgments per unit time is reduced, and hence the battery consumption of the radiation imaging cassette is reduced. After the reception of the radiography order, on the other hand, since the number of the judgments per unit time is increased, the doctor is notified of unavailability of the FPD cassette as early as possible.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

First Embodiment

Figure 1:
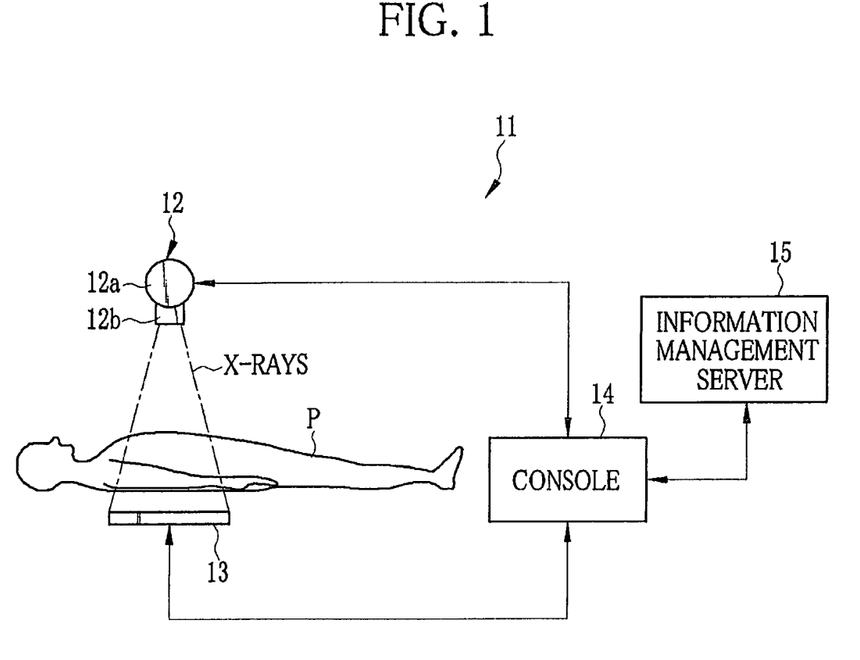
FIG. 1 is a schematic view of a radiation imaging system.

As shown in FIG. 1, a radiation imaging system 11 according to a first embodiment is constituted of a radiation generation device 12, an FPD cassette (hereinafter simply called cassette) 13, a console 14, and an information management server 15. The radiation generation device 12 applies radiation to a body part to be examined of a patient P. The cassette 13 detects the radiation that has passed through the body part. The console 14 controls the radiation generation device 12 and the cassette 13. The information management server 15 manages radiography orders that are registered on a patient-by-patient basis. The radiation generation device 12 and the cassette 13 are set up in a radiation shielded chamber or room, while the console 14 and the information management server 15 are set up in an operation room next to the radiation shielded chamber.

The radiation generation device 12 is constituted of an X-ray tube 12a for generating the radiation e.g. X-rays and a collimator 12b for limiting an irradiation field of the X-rays. The radiation generation device 12 is movably supported by a support member (not illustrated). The radiation generation device 12 is moved by the support member so as to face the cassette 13. The irradiation field of the radiation is varied in accordance with the body part to be examined, which is set by the console 14.

Figure 2:
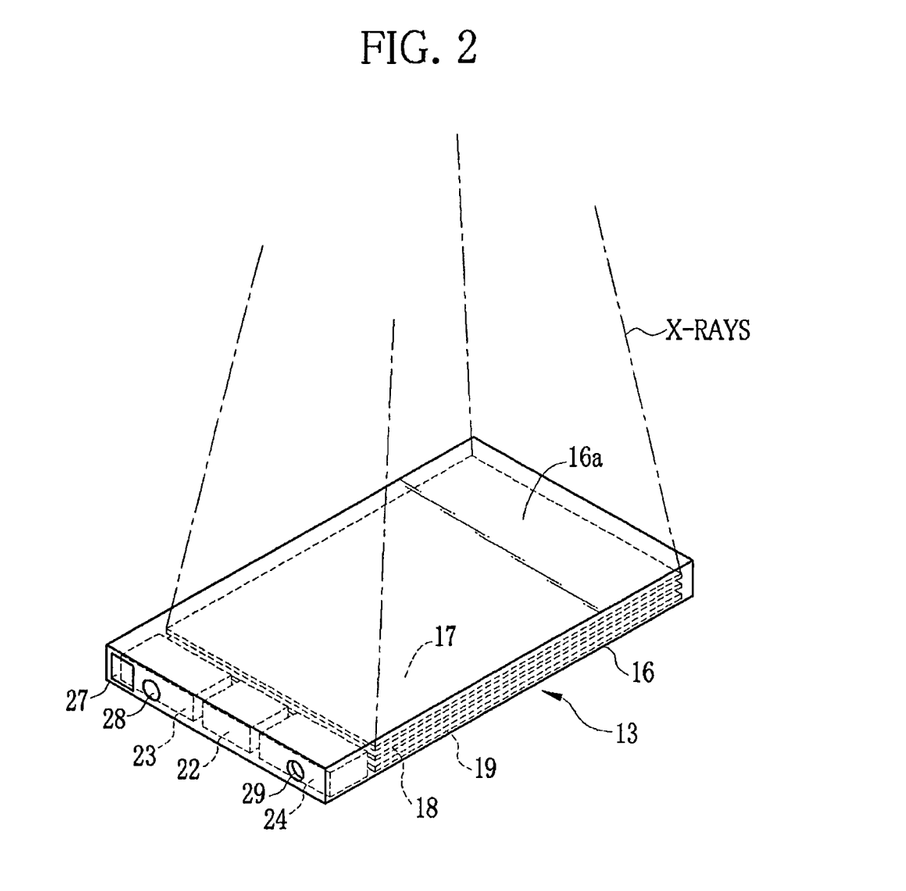
FIG. 2 is a perspective view of an FPD cassette.

As shown in FIG. 2, the cassette 13 has the same shape and size as those of a conventional IP cassette containing an IP (imaging plate), to offer high handleability and portability. Besides being used in the radiation imaging system 11 fixed in the radiation shielded chamber, the cassette 13 is sometimes brought out of the radiation shielded chamber together with a portable radiation imaging system for use in a consulting room, a ward of a hospital, or the like.

The cassette 13 is provided with a casing 16 made of a radiation transparent material. The casing 16 contains a grid 17, a radiation detector 18, and a lead plate 19 that are disposed in this order from a side of a radiation incident surface 16a of the casing 16, upon which the radiation is incident. The grid 17 removes a scattering of the radiation by the body part. The radiation detector 18 detects the radiation that has passed through the body part to be examined. The lead plate 19 absorbs a backward scattering of the radiation.

The radiation detector 18 is an indirect conversion flat panel detector (FPD) having a phosphor layer and a detecting element layer. The phosphor layer is made of a phosphor such as CsI (cesium iodide), and converts the incident radiation such as the X-rays into visible light. The detecting element layer is a two-dimensional sensor matrix of pixels. Each pixel is composed of a photodiode for converting the visible light generated in the phosphor layer into electric charge and accumulating the electric charge, and a TFT (thin film transistor) switch for controlling readout of the electric charge from the photodiode. Otherwise, the radiation detector 18 may be a direct conversion FPD, in which a conversion layer made of amorphous selenium and the like directly converts the radiation into the electric charge.

The casing 16 contains a control unit 22, a battery 23, and a communication unit 24 in addition to above. The battery 23 feeds electric power to each part of the cassette 13. The control unit 22 controls operation of the radiation detector 18. The communication unit 24 communicates with the console 14 by radio to send and receive various types of data including image data. In other words, the communication unit 24 functions as an antenna that sends and receives the various types of data.

On a side surface of the casing 16, there are provided a power switch 27, a monitor lamp 28, and a connector 29. The power switch 27 powers the cassette 13 on and off. The monitor lamp 28 indicates a power state of the cassette 13 and a charge state of the battery 23. The connector 29 is provided with a power receiving terminal (not illustrated). The connector 29 is used in charging the battery 23, in such a manner that the cassette 13 is loaded onto a cradle (not illustrated) and the power receiving terminal is connected to a power supply terminal (not illustrated) of the cradle.

Figure 3:
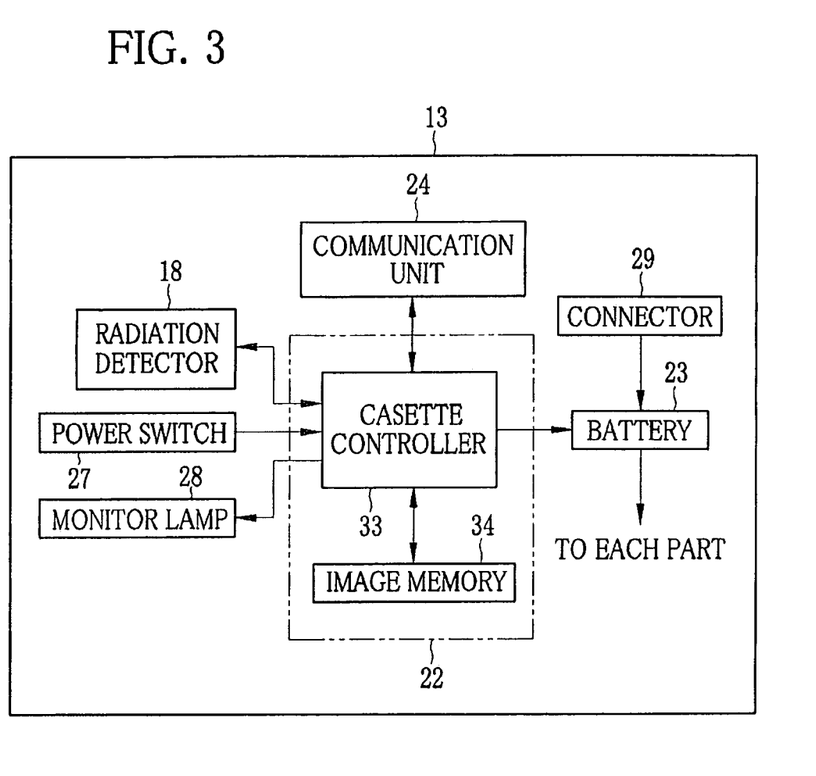
FIG. 3 is a block diagram of the FPD cassette according to a first embodiment.

As shown in FIG. 3, the control unit 22 includes a cassette controller 33 and an image memory 34. The cassette controller 33 includes a CPU for carrying out various types of computing processing, a ROM for storing control programs and control data executed by the CPU, a RAM used as a working memory of the CPU by a load of the programs and data, and the like. The cassette controller 33 overall controls each part of the cassette 13. The image memory 34 stores the image data outputted from the radiation detector 18.

Figure 4:
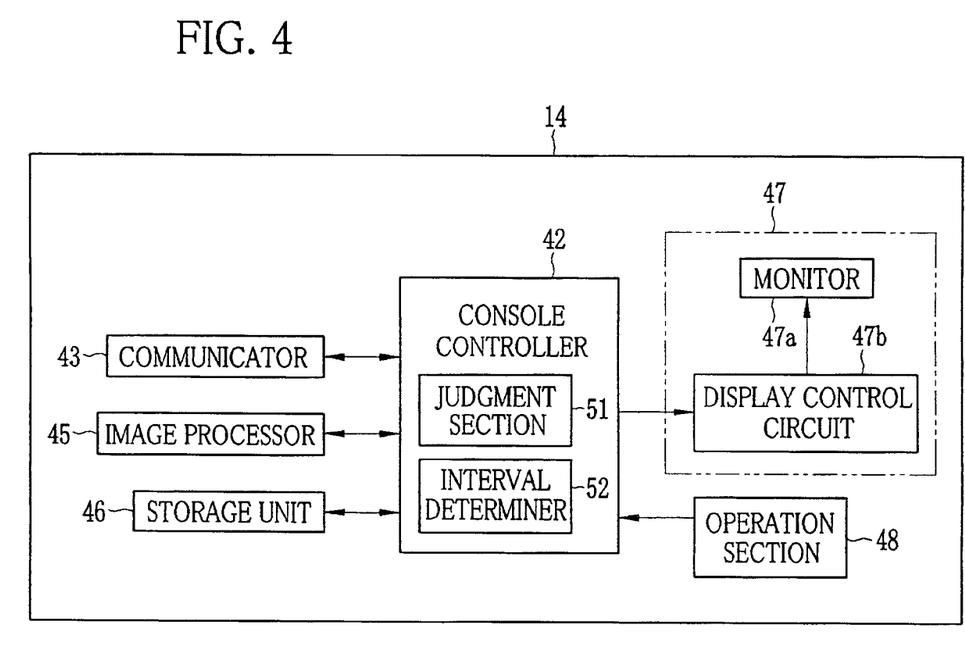
FIG. 4 is a block diagram of a console.

As shown in FIG. 4, the console 14 is constituted of a console controller 42, a communicator 43, an image processor 45, a storage unit 46, a display section 47, and an operation section 48.

As with the cassette controller 33, the console controller 42 includes a CPU for carrying out various types of computing processing, a ROM for storing control programs and control data, a RAM used as a working memory of the CPU by a load of the programs and data, and the like. The console controller 42 overall controls each part of the console 14.

The communicator 43 establishes wired or wireless communication with the radiation generation device 12, the cassette 13, and the information management server 15, to send and receive various types of data including the radiography orders and the image data.

The image processor 45 applies various types of image processing to the image data received from the cassette 13. The storage unit 46 stores the radiography orders and the image data after the image processing with being associated with each other. The display section 47 includes a monitor 47a such as an LCD, and a display control circuit 47b for displaying on the monitor 47a a radiographic image, various operation screens including a radiographic operation menu, and the like.

The operation section 48 includes a keyboard, a mouse, and the like (all of them are not illustrated), for use in various settings and operations. The operation section 48 also includes a shutter button. Upon a press of the shutter button, the radiation generation device 12 emits the radiation, and the cassette 13 detects the radiation. The doctor carries out the radiography by manipulating the operation section 48 with following instructions displayed on the monitor 47a.

The console controller 42 includes a judgment section 51 and an interval determiner 52. The judgment section 51 checks a communication state between the cassette 13 and the console 14 to judge whether or not data is transmittable therebetween. The interval determiner 52 determines intervals of judgment by the judgment section 51.

The judgment section 51 commands the communicator 43 to send a check signal for a communication check to the communication unit 24 of the cassette 13. The judgment section 51 judges based on the strength of a response signal and a response time whether or not the various types of data including the image data is transmittable, in other words, whether or not the cassette 13 and the console 14 maintain a good communication state. If the strength of the response signal is less than a predetermined threshold value, or the response time is longer than a predetermined time, the judgment section 51 judges that the cassette 13 is in a bad communication state. Otherwise, the judgment section 51 judges that the cassette 13 is in the good communication state.

If the judgment section 51 judges that the cassette 13 is in the bad communication state, the console controller 42 prohibits the radiation generation device 12 from emitting the radiation, and commands the display control circuit 47b to display abnormality in the communication state on the monitor 47a.

Under the control of the interval determiner 52, the judgment section 51 repeatedly sends out the check signals at longer time intervals before the communicator 43 receives the radiography order, and at shorter time intervals after the communicator 43 receives the radiography order. Thus, the judgment section 51 sends out the check signal and carries out the judgment once every thirty seconds before reception of the radiography order, while the judgment section 51 sends out the check signal and carries out the judgment once every three seconds after the reception of the radiography order.

Figure 5:
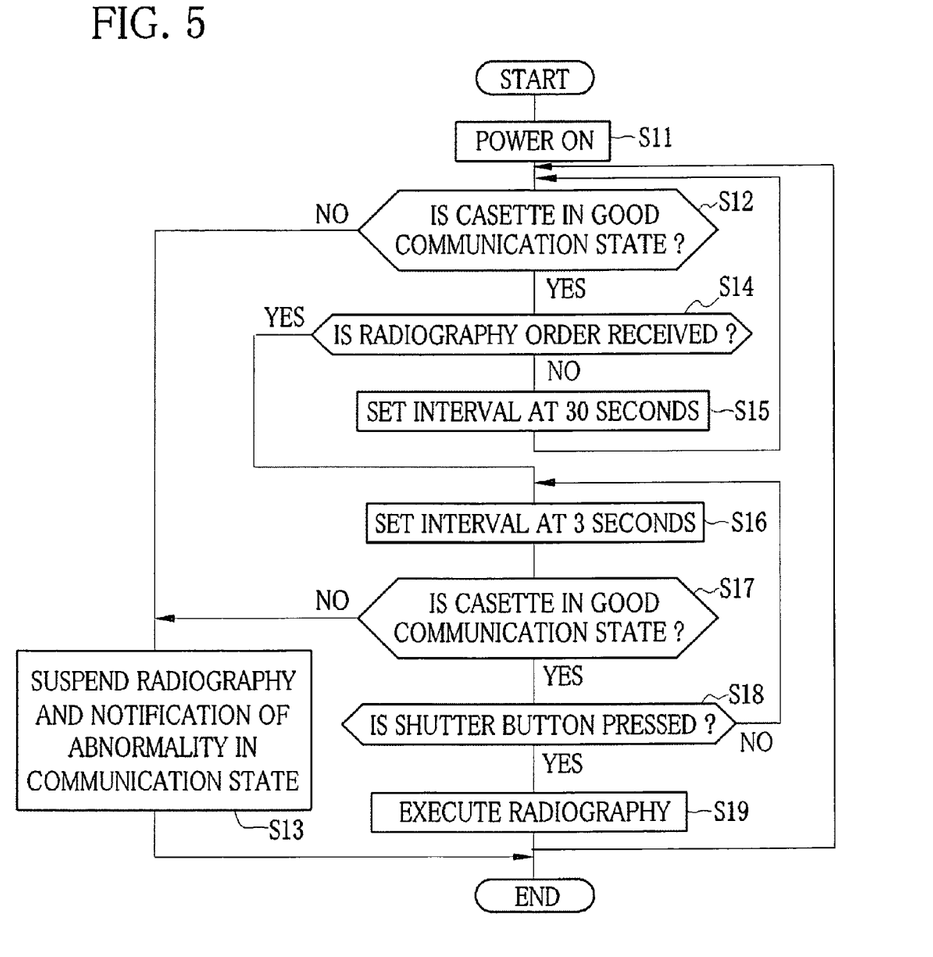
FIG. 5 is a flowchart of an operation check in the radiation imaging system.
Figure 6:
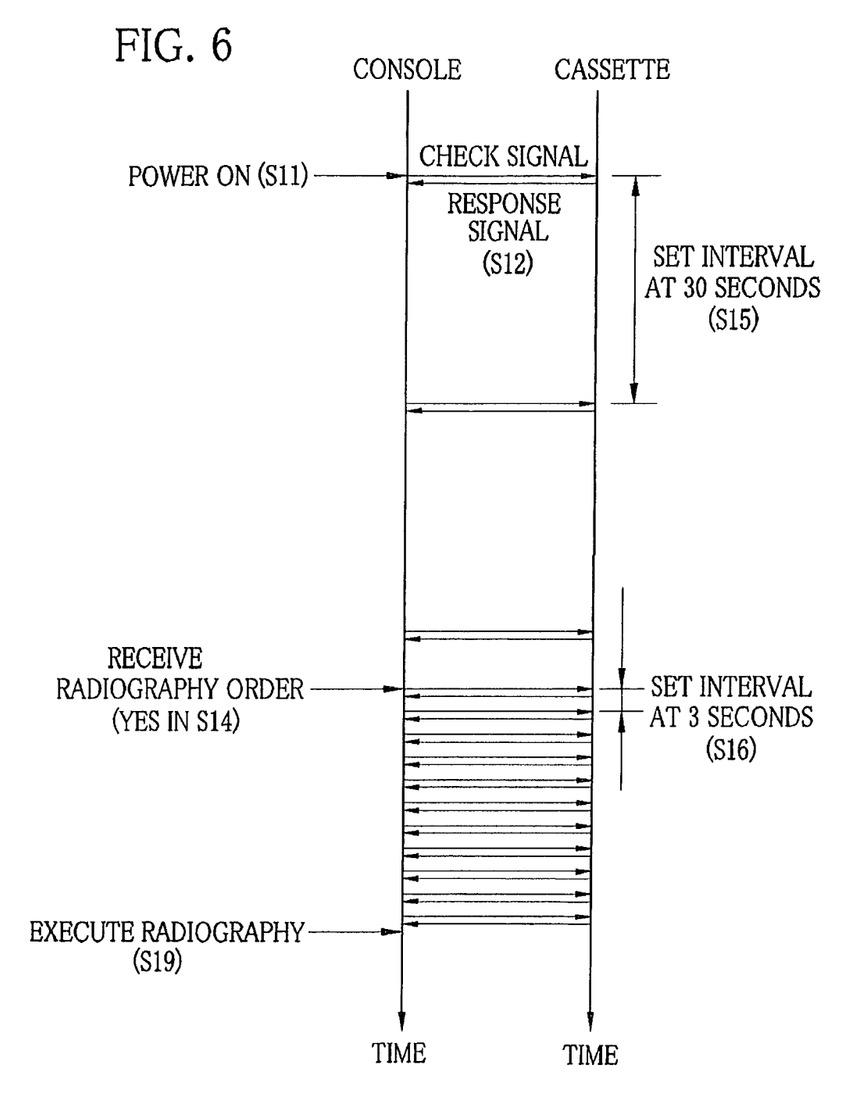
FIG. 6 is an explanatory view for explaining the timing of the operation checks in the radiation imaging system.

Next, operation of the radiation imaging system 11 having above structure will be described with referring to FIGS. 5 and 6. Upon powering on the radiation imaging system 11 (S11), the judgment section 51 of the console controller 42 sends the check signal to the cassette 13 and receives the response signal from the cassette 13 under the control of the interval determiner 52, and judges whether or not the cassette 13 is in the good communication state (S12).

If the cassette 13 is judged to be in the bad communication state (NO in S12), emission of the radiation from the radiation generation device 12 is prohibited. Also, the abnormality of the communication state is displayed on the monitor 47a (S13).

As long as the cassette 13 is judged to be in the good communication state (YES in S12), the judgment section 51 repeats the judgment of S12 at first time intervals (for example, every thirty seconds; S15) under the control of the interval determiner 52, until the radiography order is received (NO in S14).

After the reception of the radiography order (YES in S14), the judgment section 51 repeatedly carries out the same judgment as that of S12 (S17) at second time intervals (for example, every three seconds; S16) that are shorter than the first time intervals, under the control of the interval determiner 52.

If NO in S17, procedure goes to S13, as in the case of NO in S12. If YES in S17, the judgment section 51 repeats the judgment of S17 at the second time intervals (S16) under the control of the interval determiner 52, until the shutter button is pressed (YES in S18).

Upon a press of the shutter button (YES in S18), the radiation generation device 12 applies the radiation to carry out the radiography (S19). During the radiography, the judgment of the communication state of the cassette 13 is suspended. After completion of the radiography, an operation flow goes back to S12, and the judgment section 51 re-starts judging the communication state of the cassette 13 at the first time intervals (S12) under the control of the interval determiner 52.

The time of sending a first screen of the image data out of plural screens of the image data from the cassette 13 to the console 14, or the time of sending all the screens of the image data for the single patient may trigger the completion of the radiography. In quickly carrying out the radiography on a plurality of body parts or on a plurality of patients, the time of sending the first screen of the image data preferably triggers the return of the flow, so as to make preparation for the radiography on the next body part or patient, while the remaining screens of the image data are transmitted. In a case where the time of sending all the screens of the image data triggers the return of the flow, stability in the communication state is improved.

As described above, the communication state between the cassette 13 and the console 14 is repeatedly checked. If the cassette 13 is judged to be in the bad communication state, the radiation generation device 12 is prohibited from emitting the radiation, or the abnormality in the communication state is displayed on the monitor 47a. Thus, if the doctor is informed of the failure of the cassette 13 before the reception of the radiography order, the doctor can proactively deal with the failure by means of exchanging the cassette 13. If the doctor is informed of the failure of the cassette 13 after the reception of the radiography order, it is possible to prevent unnecessary exposure of the patient to the radiation.

While the communication checks are repeated at the second time intervals after the reception of the radiography order, the communication checks are repeated at the first time intervals, which are longer than the second time intervals, before the reception of the radiography order. Therefore, it is possible to reduce power consumption of the battery 23, in addition to an effect described above.

Second Embodiment

In the following second embodiment, temperature inside the casing 16 of the cassette 13 is detected to check an operating state of the cassette 13, in addition to checking the communication state between the cassette 13 and the console 14. The same structure, operation, and effect as those of the first embodiment will be omitted.

Figure 7:
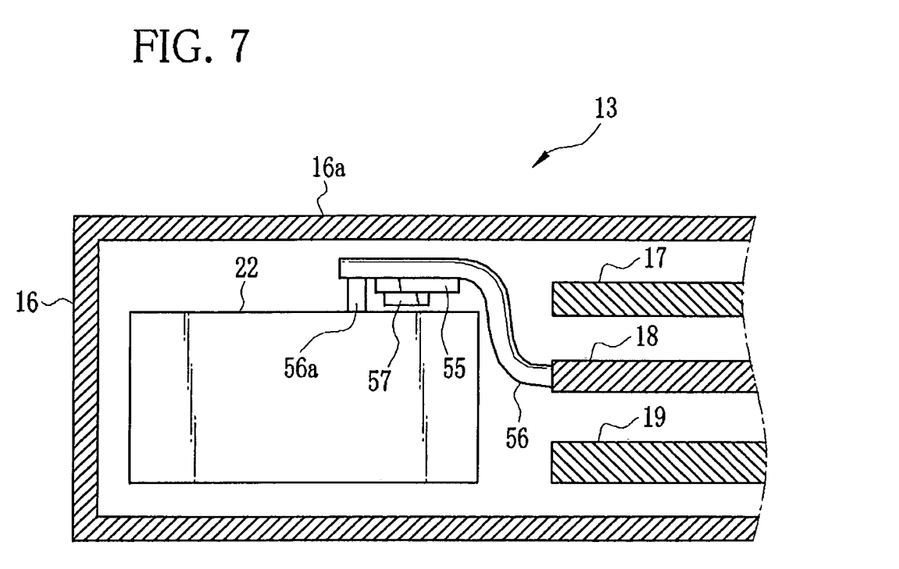
FIG. 7 is a longitudinal sectional view of the FPD cassette according to a second embodiment.

As shown in FIG. 7, the casing 16 contains an application specific integrated circuit (ASIC) 55 that functions as an amplifier and an A/D converter, a flexible cable 56 for connecting the radiation detector 18 to the control unit 22, and a thermometer 57 for detecting the temperature inside the casing 16.

The ASIC 55 is mounted in the middle of the flexible cable 56. The ASIC 55 amplifies a signal outputted from the radiation detector 18, and converts the signal from an analog format into a digital format. The flexible cable 56 is connected to the control unit 22 by a connector 56a provided at a distal end. An output signal from the ASIC 55 is inputted to the control unit 22.

Figure 8:
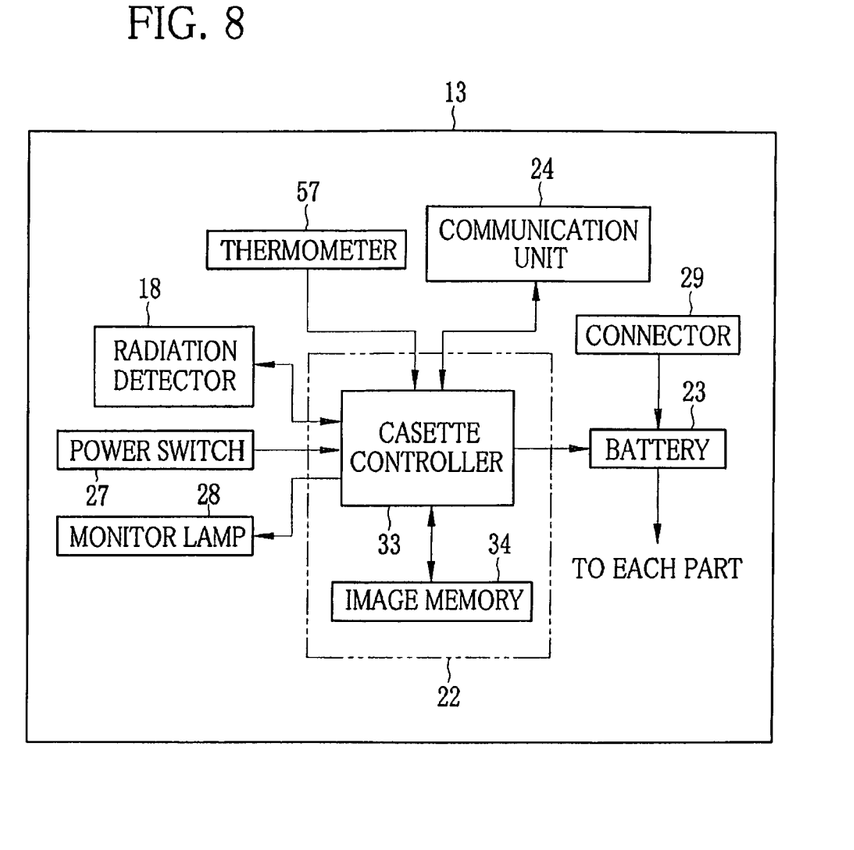
FIG. 8 is a block diagram of the FPD cassette according to the second embodiment.

As the thermometer 57, a well known thermistor, an IC temperature sensor, or the like is available. The thermometer 57 is fixed on the ASIC 55 with a thermal conductive adhesive. As shown in FIG. 8, the thermometer 57 is connected to the cassette controller 33, and outputs the detected temperature to the cassette controller 33.

The cassette controller 33 commands the communication unit 24 to send a response signal including the temperature detected by the thermometer 57 to the communicator 43 of the console 14, in response to the check signal sent from the communicator 43 of the console 14.

The judgment section 51 according to the second embodiment has the function of judging whether or not the cassette 13 is in a good operating state based on the temperature inside the casing 16, in addition to the function described in the first embodiment.

If the strength of the response signal is lower than a predetermined strength threshold value, or a response time is longer than a predetermined time, or the temperature detected by the thermometer 57 is higher than a predetermined temperature threshold value, the judgment section 51 judges that the cassette 13 is in a bad operating state. Otherwise, the judgment section 51 judges that the cassette 13 is in the good operating state.

As descried above, the operating state of the cassette 13 is checked based on the temperature inside the casing 16. Thus, the radiation generation device 12 is prohibited from emitting the radiation, in the event that ambient temperature surrounding the cassette 13 is too high, or the cassette 13 is unintentionally covered with a mat or blanket that hinders heat radiation of the cassette 13 and the temperature of the cassette 13 exceeds an operating temperature range of the cassette 13.

In the above second embodiment, the cassette is provided with the single thermometer, but may be provided with two or more thermometers. The thermometer is not necessarily directly fixed on the ASIC, but may be fixed on the ASIC through a thermal conductive part.

In addition to or instead of the communication state of the cassette and the temperature inside the casing, as described in the above first and second embodiments, various types of operating states of the cassette including a remaining battery level, a radiation detecting state, or an image data processing state may be checked.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging system comprising:
(A) a radiation imaging cassette including:
a radiation detector for detecting radiation and producing image data; and
a data sending section for sending various types of data including the image data by radio;
(B) a console including:
an order receiving section for receiving an order for radiography;
a data receiving section for receiving the image data sent from the data sending section of the radiation imaging cassette, the image data being obtained by the radiography in response to the order;
a judgment section for repeatedly judging an operating state of the radiation imaging cassette; and
an interval determiner for determining a repetition interval of the judgment by the judgment section, the interval determiner setting the repetition interval at a first time interval before the order receiving section receives the order, and the interval determiner setting the repetition interval at a second time interval after the order receiving section receives the order, the first time interval being longer than the second time interval.

2. The radiation imaging system according to claim 1, wherein the judgment section judges a communication state between the radiation imaging cassette and the console, as the operating state of the radiation imaging cassette.

3. The radiation imaging system according to claim 1, wherein the radiation imaging cassette further comprises:
a casing; and
a thermometer for measuring a temperature inside the casing,
wherein the data sending section of the radiation imaging cassette sends the temperature measured by the thermometer to the console; and
the judgment section judges the operating state of the radiation imaging cassette based on the temperature.

4. The radiation imaging system according to claim 3, wherein if the temperature is within a predetermined range, the judgment section judges that the radiation imaging cassette is in a good operating state.

5. The radiation imaging system according to claim 1, wherein
when the radiography is started, the interval determiner commands the judgment section to suspend the judgment; and
when at least first one screen of the image data out of plural screens of the image data obtained by the radiography is sent from the radiation imaging cassette to the console, the interval determiner commands the judgment section to restart the judgment at the first time interval.

6. The radiation imaging system according to claim 5, wherein when all of the plural screens of the image data are sent from the radiation imaging cassette to the console, the interval determiner commands the judgment section to restart the judgment at the first time interval.

7. A console for controlling a radiation imaging cassette, the radiation imaging cassette having a radiation detector for detecting radiation and producing image data, and a data sending section for sending various types of data including the image data by radio, the console comprising:
an order receiving section for receiving an order for radiography;
a data receiving section for receiving the image data sent from the data sending section of the radiation imaging cassette, the image data being obtained by the radiography in response to the order;
a judgment section for repeatedly judging an operating state of the radiation imaging cassette; and
an interval determiner for determining a repetition interval of the judgment by the judgment section, the interval determiner setting the repetition interval at a first time interval before the order receiving section receives the order, and the interval determiner setting the repetition interval at a second time interval after the order receiving section receives the order, the first time interval being longer than the second time interval.

8. A non-transitory computer readable medium containing executable code for controlling a radiation imaging cassette, the radiation imaging cassette detecting radiation and producing image data, comprising the steps of:
- repeatedly judging an operating state of the radiation imaging cassette;
- setting a repetition interval of the judgment at a first time interval before the reception of an order;
- receiving the order for radiography;
- setting the repetition interval of the judgment at a second time interval after the reception of the order, the second time interval being shorter than the first time interval; and
- carrying out the radiography by the radiation imaging cassette in accordance with the order.

* * * * *